(12) United States Patent
McNamara et al.

(10) Patent No.: US 6,879,851 B2
(45) Date of Patent: Apr. 12, 2005

(54) FIBER OPTIC ENDOSCOPIC GASTROINTESTINAL PROBE

(75) Inventors: Edward I. McNamara, Chelmsford, MA (US); Ron B. Lamport, Pelham, NH (US); Christopher L. Petersen, Carlisle, MA (US); Joseph M. Schmitt, Andover, MA (US)

(73) Assignee: Lightlab Imaging, LLC, Westford, MA (US)

( * ) Notice: Subject to any disclaimer, the term of this patent is extended or adjusted under 35 U.S.C. 154(b) by 75 days.

(21) Appl. No.: 09/876,834

(22) Filed: Jun. 7, 2001

(65) Prior Publication Data

US 2002/0188204 A1 Dec. 12, 2002

(51) Int. Cl.[7] ............................................... A61B 5/00
(52) U.S. Cl. ...................................... 600/407; 600/478
(58) Field of Search ................................ 600/478, 476, 600/116, 160, 182, 407

(56) References Cited

U.S. PATENT DOCUMENTS

| | | | |
|---|---|---|---|
| 4,356,731 A | 11/1982 | Mahony | 73/631 |
| 4,387,955 A | 6/1983 | Ludman et al. | 350/96.19 |
| 4,445,892 A | * 5/1984 | Hussein et al. | 604/101 |
| 5,026,131 A | 6/1991 | Jannson et al. | 350/3.7 |
| 5,090,959 A | 2/1992 | Samson et al. | 604/96 |
| 5,108,183 A | 4/1992 | Fling et al. | 356/350 |
| 5,167,233 A | 12/1992 | Eberle et al. | 128/662.06 |
| 5,188,596 A | 2/1993 | Condon et al. | 604/101 |
| 5,321,501 A | 6/1994 | Swanson et al. | 356/345 |
| 5,458,612 A | * 10/1995 | Chin | 606/192 |
| 5,459,570 A | 10/1995 | Swanson et al. | 356/345 |
| 5,759,173 A | 6/1998 | Preissman et al. | 604/96 |
| 5,908,445 A | 6/1999 | Whayne et al. | |
| 6,035,229 A | * 3/2000 | Silverstein et al. | 600/473 |
| 6,086,528 A | 7/2000 | Adair | 600/104 |
| 6,134,003 A | 10/2000 | Tearney et al. | |

FOREIGN PATENT DOCUMENTS

DE     198 59 434 A1     7/2000

OTHER PUBLICATIONS

Schmitt, J.M. et al., "An optical coherence microscope with enhanced resolving power," Optics Communication, vol. 142, pp. 203–207 (1997).

Rao, Y.J. et al., "Synthesized source for white–light sensing systems," Optics Letters, vol. 18, pp. 462–464 (1993).

* cited by examiner

*Primary Examiner*—Ruth S. Smith
(74) *Attorney, Agent, or Firm*—Testa, Hurwitz & Thibeault, LLP

(57) ABSTRACT

A fiber optic probe and a balloon catheter used in conjunction with optical imaging systems, in particular with systems which deliver and collect a single spatial mode beam, such as a single photon, a multiphoton, confocal imaging and ranging systems, such as fluorescence imaging systems.

10 Claims, 5 Drawing Sheets

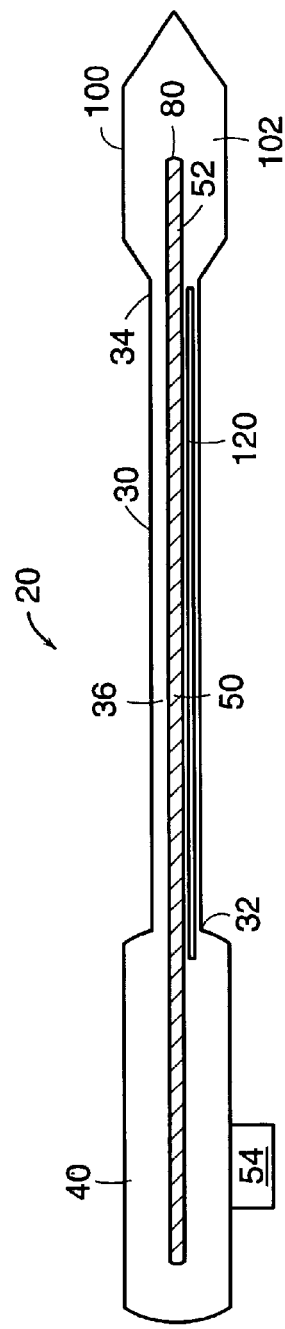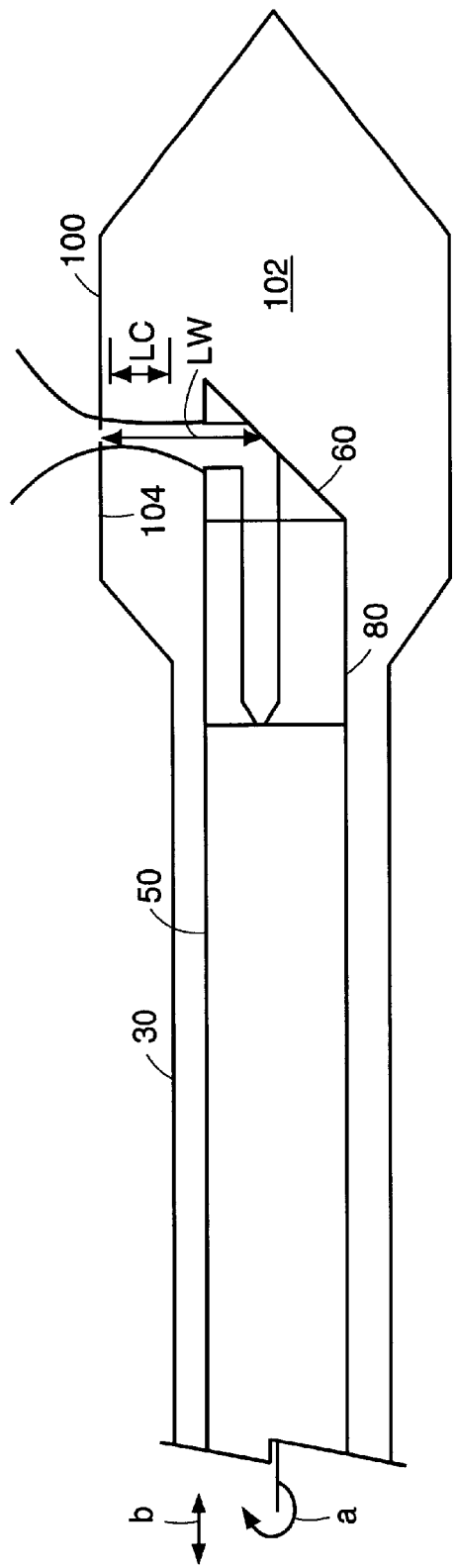

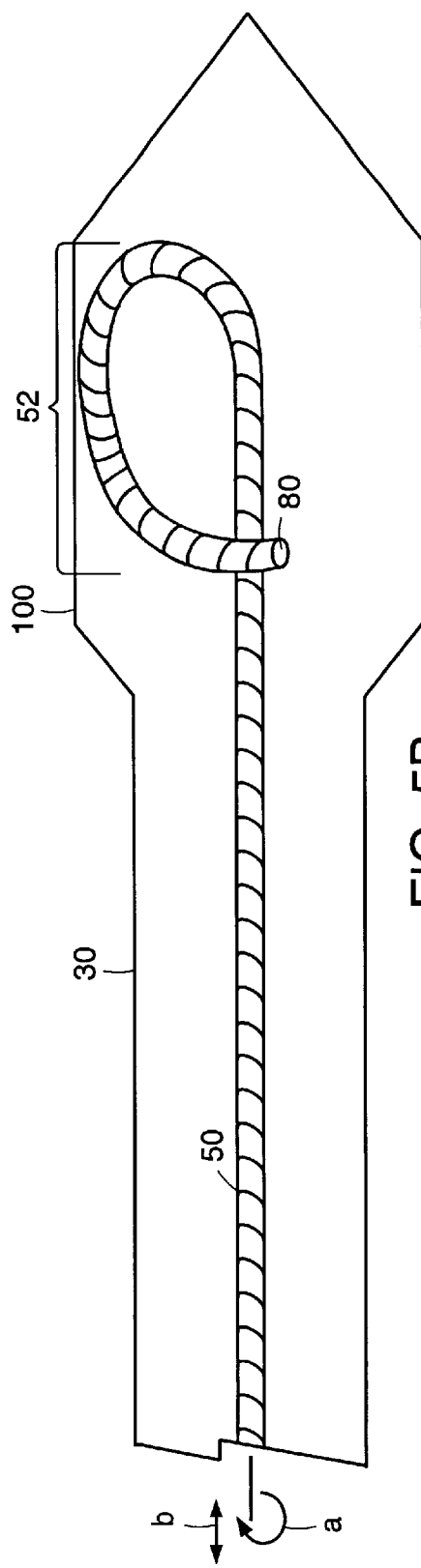
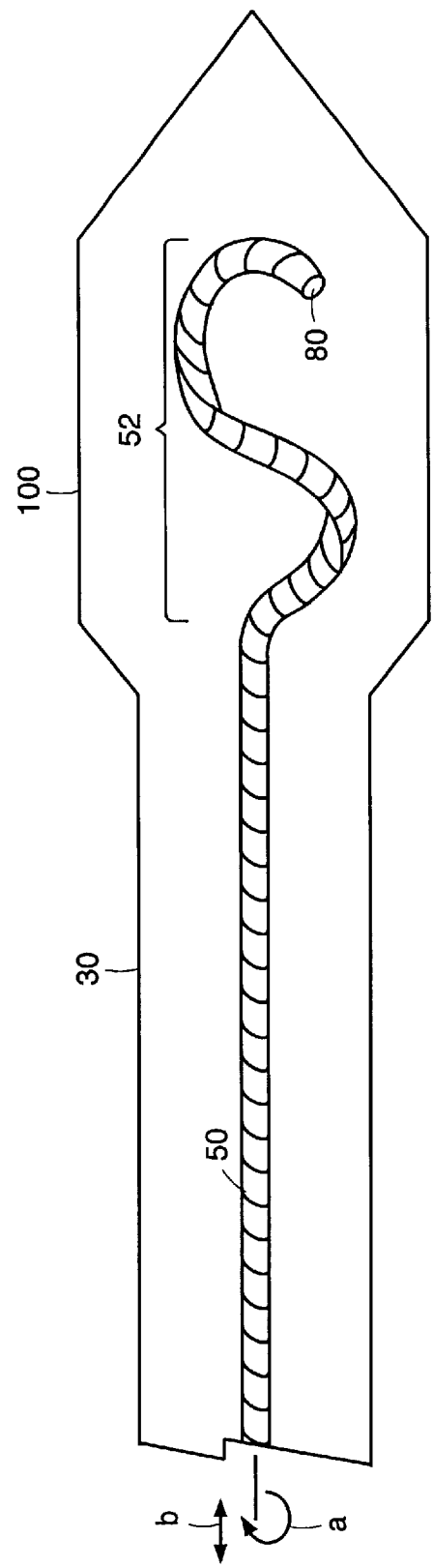

FIBER OPTIC ENDOSCOPIC GASTROINTESTINAL PROBE

STATEMENT REGARDING FEDERALLY SPONSORED RESEARCH

This invention was made with government support under a grant entitled "Development of Next-Generation OCT Technology (1998-01-0163A)," which was awarded by the National Institute of Standards and Technology, United States Department of Commerce. The U.S. government has certain rights in the invention.

FIELD OF THE INVENTION

This invention relates to the field of optical imaging and more specifically to the field of endoscopic medical imaging of the gastrointestinal system.

BACKGROUND OF THE INVENTION

Optical imaging systems such as optical coherence tomography (OCT) systems generate images or measurements by measuring the intensity of light backscattered or backreflected from a specimen and providing a gray scale or false color two-dimensional representation of this light intensity in a plane or cross-section through the object image being measured. OCT enables the non-excisional, in situ, real-time imaging of microstructure of a specimen with a resolution of approximately 2–20 microns.

An OCT system can be separated into an imaging engine and probes. The imaging engine contains the optical light source, optical interferometer and other optical detection elements, as well as electronics, motor, control(s), and computers for image generation and display. The probes are modules which are attached to the engine and direct light to and from the specimen that is to be measured or imaged.

In spite of advances in probe construction and in related delivery and scanning techniques, existing probes are not suitable for examination of tissues within lumens with a wide range of diameters. Some regions of the gastrointestinal system, such as the esophagus and duodenum, may have a diameter of 18 mm or more. Although the diameters of these structures are relatively large, the probes that fit within existing endoscopes and catheters used to examine them, are comparatively small in diameter to fit within endoscopic channels. The present invention aims to overcome these limitations.

SUMMARY OF THE INVENTION

In an aspect of the invention, a balloon catheter includes an inflatable balloon having an inner surface and a longitudinal axis, a catheter with a bore, and an optical fiber. The catheter is in communication with the balloon. The optical fiber is extendable and retractable in the bore of the catheter.

The optical fiber, according to one embodiment of the invention, has a longitudinal axis and a distal end. In one embodiment, a feature of the optical fiber includes a flexible distal end. The distal end of the optical fiber may be pre-bent into an "s" shape or spiral shape. Alternatively, a pull wire may be attached to the distal end of the optical fiber for pulling the distal end of the optical fiber so that the distal end is substantially perpendicular to the inner surface of the balloon. In a particular embodiment, the distal end of the optical fiber is substantially adjacent to an inner surface of the balloon when inflated. For example, the distance between the distal end of the optical fiber and the inner surface of the inflated balloon can be in the range of 0.01 mm to 15 mm, and preferably 1.0 mm–5.0 mm. In an embodiment of the invention, the optical fiber is rotatable, translational, or rotatable and translational, such that the distal end of the optical fiber describes a path of motion about the longitudinal axis substantially along the inner surface of the circumference of the balloon. Alternatively, the distal end of the optical fiber is moved translationally to describe a path of motion along the inner surface, substantially parallel to the longitudinal axis of the optical fiber.

In an embodiment of this aspect of the invention, the balloon of the balloon catheter has a radius between 2.5 mm–20 mm, preferably 9 mm when the balloon is inflated. The length of the catheter is 5 cm to 200 cm, and more preferably 10–110 cm. In a particular embodiment of the invention, a guidewire is joined to the distal end of the balloon catheter.

BRIEF DESCRIPTION OF THE DRAWINGS

FIG. 1 illustrates a highly schematic plan view of one embodiment of an endoscopic balloon catheter device according to the invention.

FIG. 2 illustrates an embodiment of the invention including a rotating optical beam director.

FIG. 5A illustrates another embodiment of the invention.

FIG. 5B illustrates another embodiment of the invention.

DETAILED DESCRIPTION OF THE INVENTION

Figure 3A:
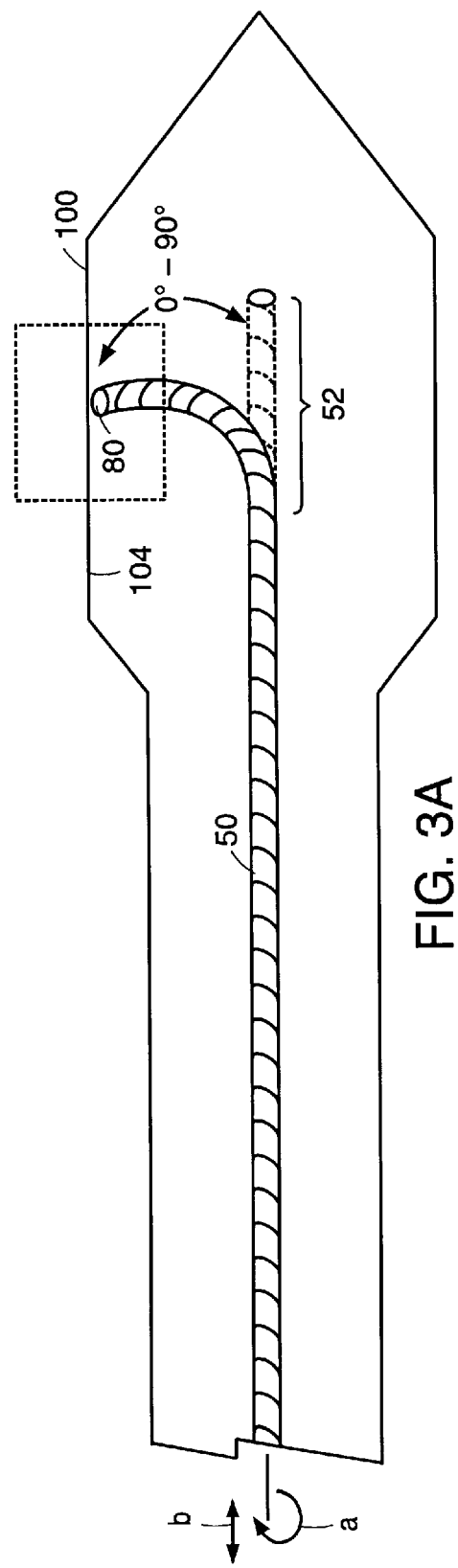
FIG. 3A illustrates an embodiment of the invention including a flexible optical fiber.

As described below, a fiber optic endoscopic gastrointestinal probe according to the invention, can be used in conjunction with a number of different types of optical imaging systems, in particular with systems which deliver and collect a single spatial mode beam such as a single photon, a multiphoton, confocal imaging and ranging systems such as fluorescence imaging system. OCT is the preferred imaging technology to be used in the fiber optic endoscopic gastrointestinal probe described herein.

In the preferred embodiment of the invention, the fiber optic endoscopic gastrointestinal probe communicates with the imaging engine of an OCT device by means of a single mode optical fiber housed within the gastrointestinal probe. Used in conjunction with an OCT imaging system, the fiber optic endoscopic gastrointestinal probe of the invention enables the tomographic imaging of the microstructure of internal organs and tissues in a living subject.

Referring to FIG. 1, shown is an embodiment of a fiber optic endoscopic gastrointestinal probe 20 of the invention. In general, the probe includes a handle 40, a catheter 30, an optical fiber 50, a scanning mechanism 54, and a balloon 100. The catheter 30, optical fiber 50, and balloon 100 are dimensioned for insertion into the body. For example, the fiber optic endoscopic gastrointestinal probe 20 is sized for insertion into the gastrointestinal tract, or a duct, such as the cystic duct of a patient. The fiber optic endoscopic gastrointestinal probe 20 of the invention ranges from about 5 cm to 200 cm in length, and more preferably about 10 cm to 110 cm.

With continued reference to FIG. 1, a long, small diameter optical fiber or fiber bundle 50 extends through bore 36 of the catheter 30. The catheter 30 has a proximal end 32 closest to the operator, and a distal end 34 which is inserted into the body of a patient. The catheter 30 is made of material that is sufficiently flexible to permit an operator to maneuver the catheter 30 into a body tract, and sufficiently rigid to prevent the catheter 30 from collapsing as the catheter 30 is moved in the body tract.

Still referring to FIG. 1, disposed on the distal end 34 of the catheter 30 is an annular balloon 100. A guidewire (not shown) may optionally be attached to the distal end of the catheter 30. Balloon 100 is filled via port 120 which communicates with the lumen 102 of the balloon. The lumen 102 may be filled with air, water, deuterated water or other fluid or gaseous substance that is substantially transparent to the OCT probe illumination. The diameter of the balloon ranges from about 5 to 40 mm in the expanded state, preferably about 18 mm. The materials used to construct the balloon 100 are substantially transparent to the selected wavelengths of light used to image structures in the body surrounding the balloon 100. For example, the balloon 100 may be constructed of nylon, PET (polyethylene terephthalate), PE (polyethylene), PEBAX™ (Atochem Corp.; France) (polyethylene block amide), other thermoplastics, and more.

Within the bore 36 of the catheter 30 resides the optical fiber 50, which is, in one embodiment, a flexible single mode optical fiber or a single mode fiber optic bundle, either of which may be of the type known as "polarization maintaining," depending on the specific application. The use of a single mode optical fiber, for example, is preferable for applications of OCT imaging because it will propagate and collect a single transverse spatial mode optical beam which can be focused to its minimum spot size for a desired application, and single-mode wavefronts are well suited for OCT detection.

In one embodiment, the catheter 30 with optical fiber 50 may be translationally or rotationally moveable, or both, within the balloon 100. In another embodiment, the catheter 30, optical fiber 50, and balloon 100 comprise a single, integrated unit, moveable as one. A transparent window or a lens 80 such as a GRIN lens or micro lens is positioned at the distal end 52 of optical fiber 50 to permit the focusing of light onto and receiving backscatter from the structures surrounding the balloon 100.

In a particular embodiment of the invention, a beam director 60, illustrated in FIG. 2, is positioned within the lumen 102 of the balloon 100 in close juxtaposition to the distal end of the optical fiber 50 to direct light from the optical fiber 50 to the structure being imaged. The optical beam director 60, in one embodiment, may be translated longitudinally, rotated, or both. Alternatively, the optical beam directing system 60 is directly coupled to the distal end of a translationally moveable or rotatable single mode optical fiber and is positioned to transmit the optical radiation from the single mode optical fiber to the structure and to transmit reflected optical radiation from the structure to the single mode optical fiber. The optical fiber may be simultaneously translationally moveable and rotatable. In one embodiment, the beam director 60 directs light from the distal end 52 of the optical fiber 50 in a direction substantially perpendicular to the inner surface 104 of the balloon 100. The beam director 60 may include a prism, a lens, a diffraction grating, or a turning mirror and may be driven from a motor external to the device 20 via a mechanical linkage or may be driven via a micromotor.

Referring still to FIG. 2, in this embodiment, the confocal length "Lc" of the lens 80 is about 0.5 to 4 cm, preferably about 1–3 cm. In a particular embodiment, the lens 80 is a GRIN lens coupled to a turning prism. Alternatively, the lens is a multi-mode fiber of a length determined by the application. Alternatively, a piece of cladless fiber angle polished and attached to the lens 80 may be used as a turning mirror.

Figure 3B:
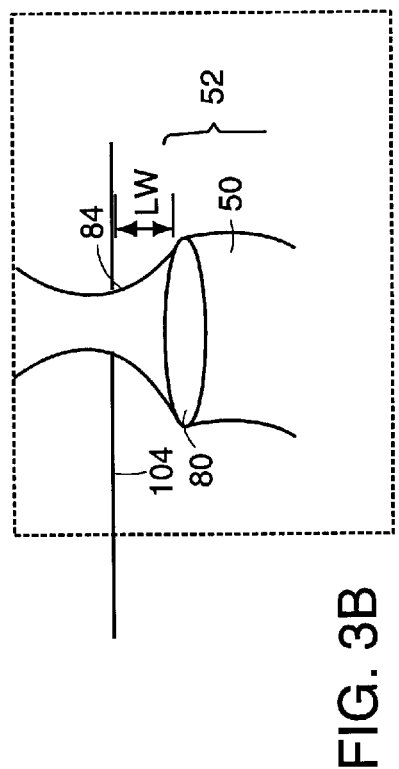
FIG. 3B illustrates an enlargement of the boxed area of FIG. 3A.

Referring now to FIG. 3A, in another embodiment of the invention, the distal end 52 of optical fiber 50 can be flexed from 0° (shown in phantom in FIG. 3A) to any acute angle up to about 90° from the long axis of the catheter 30. In the flexed position, the distal end 52 of optical fiber 50 is preferably oriented perpendicular to the long axis of the inner surface 104 of the balloon 100. The lens 80 at the distal end of the optical fiber 50 is thereby located a distance "Lw" from the balloon wall for maximal performance based on the focal length "Lc" of the lens 80, best illustrated in FIG. 3B. Because of the short working distance "Lw" between the lens 80 and the inner surface 104 of balloon 100, the diameter of the lens 80 can be small. Furthermore, little loss of signal from the media filling the balloon 100 occurs since the beam 84 being so close to the balloon wall travels only a short distance through the media. Distance "Lw" ranges from about 0.01 mm to 15 mm, and preferably 1.0 mm to 5.0 mm.

The optical fiber 50 in one embodiment is rotatable such that the distal end 52 of the optical fiber 50 describes a path of motion indicated by arrow (a) substantially along the inner surface 104 of the inflated balloon 100. In another embodiment, the optical fiber 50 is translationally moveable such that the distal end 52 of the optical fiber describes a path of motion indicated by arrow (b) substantially parallel to the long axis along the inner surface 104 of the balloon 100. In yet another embodiment, optical fiber 50 is both rotationally and translationally moveable.

Figure 4:
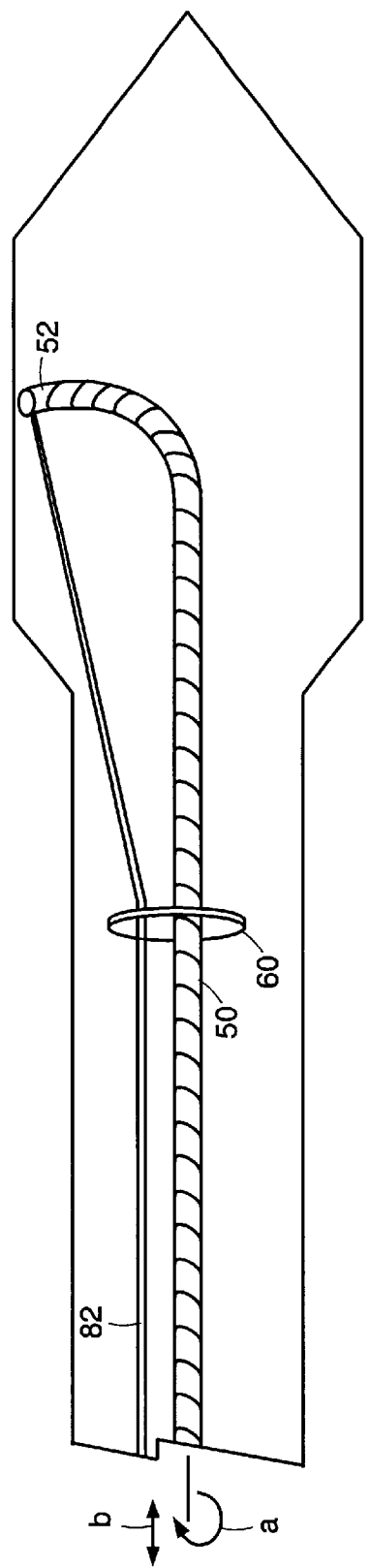
FIG. 4 illustrates an embodiment of the invention including a pull wire.

An embodiment of the invention can also feature a pull wire 82, illustrated in FIG. 4. Pull wire 82, such as a nitinol wire, is joined at one end to the distal end 52 of the optical fiber 50, passes through ring structure 60, and extends to the proximal end of the device. An operator, by pulling on pull wire 82, causes the distal end 52 of the optical fiber 50 to bend 0°–90° from the long axis of the catheter.

In yet another embodiment according to the invention, the distal end 52 of optical fiber 50 is "s" shaped, or spiral shaped, illustrated in FIG. 5A, or may turn 360° on itself, as illustrated in FIG. 5B. Alternatively, a turning mirror (not shown) is placed adjacent the lens. In this embodiment, the fiber could be bent less than 90°. In all of these embodiments, imaging occurs as the optical fiber 50 is rotated along its long axis or moved translationally within the bore 36 of the catheter 30.

Figure 6:
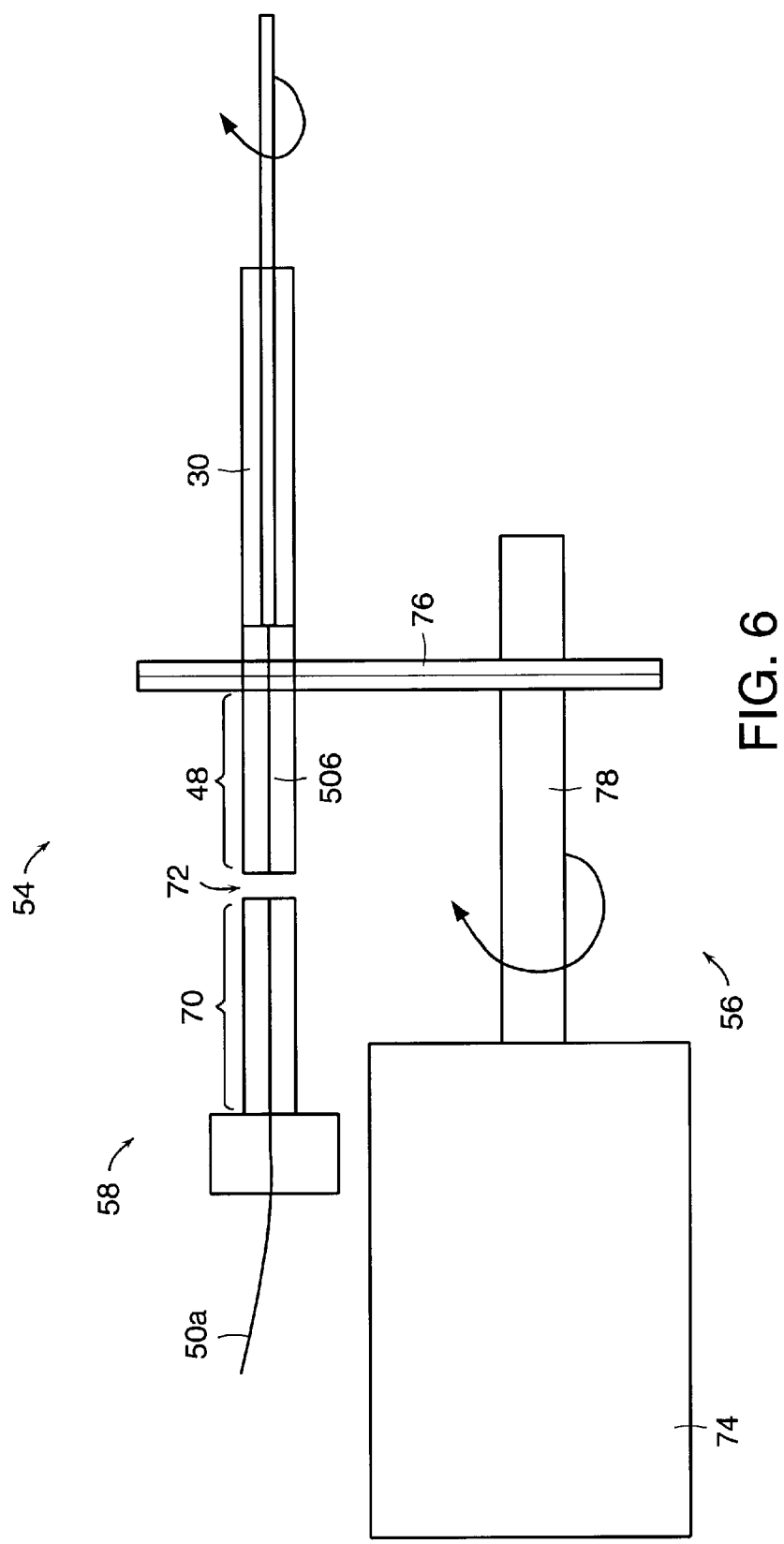
FIG. 6 illustrates an embodiment of the invention including a rotational scanning mechanism.

In a particular embodiment, the optical fiber 50 is rotatable. Referring to FIG. 6, one embodiment of a rotational scanning mechanism 54 typically includes a rotation mechanism 56 and an optical coupling system 58. The optical fiber bundle 50 terminates within the coupling system 58. The coupling system 58 includes a coupling member 70 which is spaced by an interface 72 from an optical connector 48. The interface 72 is used to terminate optical radiation from the input optical fiber 50a to the optical fiber extending within catheter 30. The coupling member 70 can be physically coupled to the optical connector 48 or, as shown, can be separated by an air or a fluid medium formed in the interface 72. In the event that the coupling member 70 is physically coupled to the optical connector 48, the coupling member 70 can be removed from the optical connector 48, thereby enabling the catheter 30 to be replaced with each patient.

The optical connector 48 functions as the drive shaft for the optical fiber 50 as the rotation mechanism is coupled thereto. The rotation mechanism includes a DC or AC drive motor 74 and a gear mechanism 76 having predetermined gear ratios. The gear mechanism 76 is coupled to the motor 74 via a shaft 78. Upon activation of the drive motor 74, the shaft 78 rotates causing gear mechanism 76 and rotatable optical fiber 50 to rotate. Alternatively, the DC motor can be a micromotor (not shown) causing rotation of optical fiber 50.

While the present invention has been described in terms of certain exemplary preferred embodiments, it will be readily understood and appreciated by one of ordinary skill in the art that it is not so limited and that many additions, deletions and modifications to the preferred embodiments may be made within the scope of the invention as hereinafter claimed. Accordingly, the scope of the invention is limited only by the scope of the appended claims.

What is claimed is:

1. A balloon catheter comprising:

an inflatable balloon having an inner surface;

a catheter having a longitudinal axis and a bore, said bore in communication with said balloon; and an optical fiber, positioned within said bore, and having a lens positioned at a distal end of said optical fiber, said lens positioned at a working distance from said inner surface of said balloon and said distal end oriented substantially at an acute angle as measured from said longitudinal axis of said catheter to said inner surface of said balloon;

wherein said fiber is capable of transmitting light having a predetermined distribution of wavelengths, and wherein said balloon is transparent to at least a portion of said distribution of wavelengths of light.

2. The balloon catheter of claim 1 wherein said optical fiber is rotatable such that said distal end of said optical fiber describes a path of motion about said long axis of said catheter substantially along said inner surface of said balloon.

3. The balloon catheter of claim 1 wherein said optical fiber is translationally moveable such that said distal end of said optical fiber describes a path of motion substantially parallel to said long axis of said catheter.

4. The balloon catheter of claim 1 wherein the balloon has a radius between 2.5 mm and 20 mm when inflated.

5. The balloon catheter of claim 1 wherein said balloon when uninflated and said optical fiber are dimensioned to fit within said catheter.

6. The balloon catheter of claim 1 wherein said working distance is about 1.0 to about 5.0 mm.

7. The balloon catheter of claim 1 wherein said distal end of said optical fiber is flexible.

8. The balloon catheter of claim 7 further comprising a pullwire wherein said pullwire is operably joined to said distal end of said optical fiber.

9. The balloon catheter of claim 1 wherein said lens comprises a GRIN lens.

10. A balloon catheter comprising:

an inflatable balloon having an inner surface, a lumen, and a diameter between about 2.5 mm and 20 mm when inflated;

a catheter having a bore in communication with said lumen of said balloon; and an optical fiber, positioned within said bore, and having a GRIN lens positioned at a distal end of said optical fiber, said GRIN lens positioned within about 1.0 mm to about 5.0 mm from said inner surface of said balloon when inflated, said optical fiber being rotatably and translationally moveable relative to said catheter;

wherein said fiber is capable of transmitting light having a predetermined distribution of wavelengths, wherein said balloon is transparent to at least a portion of said distribution of wavelengths of light, and wherein said optical fiber, when moved translationally and rotationally, focuses said light onto and receives backscatter from structures substantially adjacent to the exterior of said balloon.

* * * * *

UNITED STATES PATENT AND TRADEMARK OFFICE
CERTIFICATE OF CORRECTION

| | | |
|---|---|---|
| PATENT NO. | : 6,873,851 B2 | Page 1 of 1 |
| APPLICATION NO. | : 09/876834 | |
| DATED | : March 29, 2005 | |
| INVENTOR(S) | : Michael Wayne Brown, Rabindranath Dutta and Michael A. Paolini | |

It is certified that error appears in the above-identified patent and that said Letters Patent is hereby corrected as shown below:

<u>Column 16</u>, line 25, delete "location at" and add -- location of -- .

<u>Column 17</u>, line 37, delete "indicating location" and add -- indicating a location -- .

<u>Column 18</u>, line 49, delete "record" and add -- records -- .

<u>Column 19</u>, line 28, delete "providing plurality" and add -- providing a plurality -- .
Line 28, delete "record" and add -- records -- .
Line 64-65, delete "least of the of the" and add -- least one of the-- .

<u>Column 20</u>, line 10, delete "end" and add -- and -- .
Line 38, delete "from determined" and add -- from the determined -- .
Line 56, delete "for personal" and add -- for a personal -- .
Line 58, delete "providing plurality" and add -- providing a plurality -- .
Line 61, delete "alocation" and add -- a location -- .

<u>Column 21</u>, line 3, delete "device wherein" and add -- device, wherein -- .
Line 5, delete "devices, within" and add -- devices within -- .
Line 58, delete "device" and add -- devices -- .

Signed and Sealed this

Ninth Day of January, 2007

JON W. DUDAS
*Director of the United States Patent and Trademark Office*